United States Patent [19]

Deibel

[11] Patent Number: Plant 5,497

[45] Date of Patent: Jun. 18, 1985

[54] POINSETTIA PLANT NAMED V-14 HOT PINK

[75] Inventor: Dennis Deibel, Crestwood, Ky.

[73] Assignee: Paul Ecke, Jr., Encinitas, Calif.

[21] Appl. No.: 510,423

[22] Filed: Jul. 1, 1983

[51] Int. Cl.[3] ..... A01H 5/00

[52] U.S. Cl. ..... Plt./86

[58] Field of Search ..... Plt./86

*Primary Examiner*—Robert E. Bagwill

*Attorney, Agent, or Firm*—Charles W. Rummler

[57] ABSTRACT

A new poinsettia cultivar having the principal growth characteristics of the red variety named V-14 (U.S. Plant Pat. No. 4,384) and the pink variety named V-14 Pink (U.S. Plant Pat. No. 4,808), which is a sport of V-14, including the ability to produce numerous side shoots on its stems and to produce bracts with short petioles, but particularly distinguished by its bracts which have a unique and distinctive "hot pink" color as compared with those of the said V-14 Pink.

1 Drawing Figure

BACKGROUND OF THE NEW PLANT

This new poinsettia plant originated as a new mutation of the red poinsettia variety named V-14, U.S. Plant Pat. No. 4,384, grown in greenhouse at Crestwood, Ky., and was discovered by me in the course of my work with commercial culture of the parent variety. I selected this particular plant for propagation because of its distinctive and novel "hot pink" color and it was reproduced by me, by means of cuttings, to observe its growth characteristics and its retention of the novel color in its bracts. Successive propagations of this new plant, by cuttings, both at Crestwood, Ky., and at Encinitas, Calif., has demonstrated that its distinctive color characteristic holds true from generation to generation and appears to be firmly fixed.

DESCRIPTION OF THE DRAWINGS

This new poinsettia cultivar is illustrated by the accompanying photographic drawing, which shows blooms of the new variety in side-by-side display with typical blooms of the variety V-14 Pink (U.S. Plant Pat. No. 4,808) which is also a mutation of U.S. Plant Pat. No. 4,384 and which appear at the left side of the drawing, one bloom of each variety having been hand painted to show the true colors.

DESCRIPTION OF THE NEW PLANT

The following is a detailed description of this new poinsettia plant, as observed in greenhouse at Encinitas, Calif., with the color designations according to The R.H.S. Colour Chart published by The Royal Horticultural Society of London, England.

THE PLANT

Origin: Mutation.

Parentage: Poinsettia V-14 (U.S. Plant Pat. No. 4,384).

Classification:

*Botanic.*—*Euphorbia pulcherrima.*

*Commercial.*—Greenhouse poinsettia.

Form: Shrub.

Height: Medium.

Growth habit: Upright and vigorous with self-branching side shoots.

Growth rate: Very fast. Rooting occurs in about fifteen days or less under automatic mist with the plant blooming in about nine weeks at a night temperature of about 18° C.

Foliage: Alternate and horizontal, with medium persistence and in normal abundance.

*Leaf size.*—Medium, about 4 to 6 inches long and about $2\frac{1}{2}$ to $4\frac{1}{2}$ inches wide.

*Leaf shape.*—Substantially ovate, some with acuminate tip. Most leaves have one or two serrations on each side of the petiole.

*Aspect.*—Upper side — Dull with vein indented. Under side — Dull with ordinary veining.

*Color.*—Upper side — Dark Green, between 146A and 147A. Under side — Dark Green, near 146B.

*Retention.*—The foliage lasts well when kept at a low room temperature, i.e., below 20° C., and with good light intensity.

Bracts: The bracts of this new plant are similar to those of other poinsettias, particulary to those of the V-14 family, except for the differences of color. The color of the bracts of this new poinsettia may generally be described as hot pink in that the coloration is somewhat brighter than that of the earlier pink mutation of V-14. The bract presentation of this new plant, however, is more full and uniform in appearance as illustrated by the three blooms at the right hand side of the view.

*Size.*—Various, up to 7 inches long and 6 inches wide, some being as wide as they are long.

Shape.—Ovate-acuminate with substantially entire margins but some with dentations. Small bracts are elliptic in shape.

Petioles.—Quite short, from about $\frac{1}{4}$ inch to about 1 inch long.

*Color.*—Young bracts — Near R.H.S. 52B, but slightly greyed. Older and larger bracts — Slightly lighter in color more toward R.H.S. 52C but slightly greyed. Under side of the bracts — Near R.H.S 48C.

*Ribs and veins.*—As the bracts become older and larger, the veins become more prominent and darker, near R.H.S. 50A, in color. Veins on the under side of the bracts are much the same color as 48C with the midrib tending toward a cream color.

*Retention.*—The foliage lasts very well when kept at a low room temperature, i.e., below 20° C., and with good light intensity.

In general, this new poinsettia cultivar, with the exception of its bract coloration, has all of the extra-ordinary and advantageous growth characteristics and habits of its red parent V-14 (U.S. Plant Pat. No. 4,384) and about the same as those of its nearest variety V-14 Pink (U.S. Plant Pat. No. 4,808). The rich pink coloration of this new poinsettia and the full, close display of its bracts make this a most unique and attractive plant.

I claim:

1. A new and distinctive poinsettia cultivar, substantially as herein shown and described, distinguished by the warm and deep pink coloration of its bracts which are tightly centered and present a very compact display.

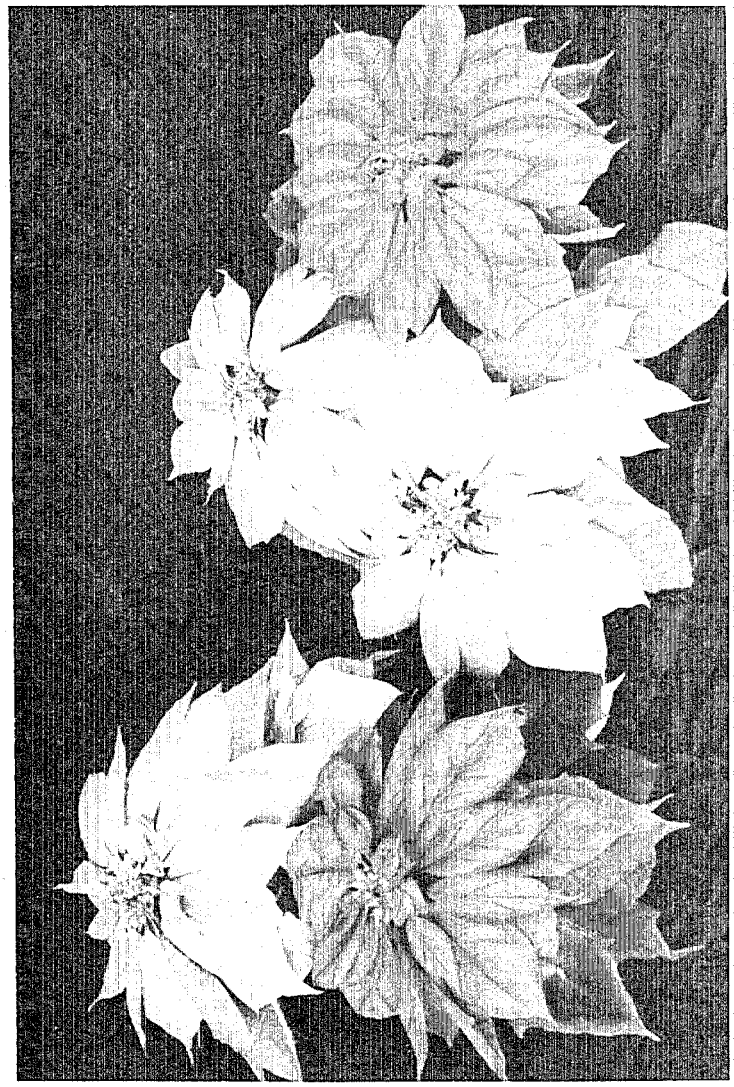

* * * * *